US007579174B2

(12) United States Patent
Bailey et al.

(10) Patent No.: US 7,579,174 B2
(45) Date of Patent: *Aug. 25, 2009

(54) ENHANCED PRODUCTION OF LIPIDS CONTAINING POLYENOIC FATTY ACID BY VERY HIGH DENSITY CULTURES OF EUKARYOTIC MICROBES IN FERMENTORS

(75) Inventors: Richard B. Bailey, Del Mar, CA (US); Don DiMasi, San Diego, CA (US); Jon M. Hansen, Chula Vista, CA (US); Peter J. Mirrasoul, San Diego, CA (US); Craig M. Ruecker, San Diego, CA (US); George T. Veeder, III, Ramona, CA (US); Tatsuo Kaneko, San Diego, CA (US); William R. Barclay, Boulder, CO (US)

(73) Assignee: Martek Biosciences Corporation, Columbia, MD (US)

( * ) Notice: Subject to any disclaimer, the term of this patent is extended or adjusted under 35 U.S.C. 154(b) by 136 days.

This patent is subject to a terminal disclaimer.

(21) Appl. No.: 11/352,421

(22) Filed: Feb. 10, 2006

(65) Prior Publication Data
US 2006/0286648 A1 Dec. 21, 2006

Related U.S. Application Data

(63) Continuation of application No. 10/371,394, filed on Feb. 21, 2003, now abandoned, which is a continuation of application No. 09/771,352, filed on Jan. 26, 2001, now Pat. No. 6,607,900.

(60) Provisional application No. 60/178,588, filed on Jan. 28, 2000.

(51) Int. Cl.
C12P 7/64 (2006.01)
C12N 1/14 (2006.01)
(52) U.S. Cl. ............... 435/134; 435/254.1; 435/911
(58) Field of Classification Search ............... None
See application file for complete search history.

(56) References Cited

U.S. PATENT DOCUMENTS

| 5,130,242 | A | 7/1992 | Barclay |
| 5,244,921 | A | 9/1993 | Kyle et al. |
| 5,340,594 | A | 8/1994 | Barclay |
| 5,340,742 | A | 8/1994 | Barclay |
| 5,492,938 | A | 2/1996 | Kyle et al. |
| 5,698,244 | A | 12/1997 | Barclay |
| 6,140,486 | A | 10/2000 | Facciotti et al. |
| 6,255,505 | B1 | 7/2001 | Bijl et al. |
| 6,403,345 | B1 | 6/2002 | Kiy et al. |
| 6,410,281 | B1 | 6/2002 | Barclay |
| 6,433,152 | B1 | 8/2002 | Lang et al. |
| 6,451,567 | B1 | 9/2002 | Barclay |
| 6,509,178 | B1 | 1/2003 | Tanaka et al. |
| 6,582,941 | B1 | 6/2003 | Yokochi et al. |
| 6,596,766 | B1 | 7/2003 | Igarashi et al. |
| 6,607,900 | B2 | 8/2003 | Bailey et al. |
| 2003/0180898 | A1 | 9/2003 | Bailey et al. |
| 2006/0286649 | A1 | 12/2006 | Bailey et al. |
| 2008/0032360 | A1 | 2/2008 | Bailey et al. |
| 2008/0032361 | A1 | 2/2008 | Bailey et al. |
| 2008/0032362 | A1 | 2/2008 | Bailey et al. |
| 2008/0032363 | A1 | 2/2008 | Bailey et al. |
| 2008/0032364 | A1 | 2/2008 | Bailey et al. |
| 2008/0032365 | A1 | 2/2008 | Bailey et al. |
| 2008/0032366 | A1 | 2/2008 | Bailey et al. |
| 2008/0032381 | A1 | 2/2008 | Bailey et al. |
| 2008/0032387 | A1 | 2/2008 | Bailey et al. |
| 2008/0057551 | A1 | 3/2008 | Bailey et al. |

FOREIGN PATENT DOCUMENTS

| CA | 2563427 | 10/2005 |
| DE | 19838011 | 5/1999 |
| DE | 102004017370.2 | 10/2005 |
| EP | 193926 | 9/1986 |
| EP | 0823475 | 2/1998 |
| EP | 1024199 | 8/2000 |
| JP | WA H05-503425 | 6/1993 |
| JP | WA H05-505726 | 8/1993 |
| JP | A H09-000284 | 1/1997 |
| JP | A H09-065871 | 3/1997 |
| JP | A H11-285376 | 10/1999 |
| WO | WO 91/11918 | 8/1991 |
| WO | WO 91/14427 | 10/1991 |
| WO | WO 92/13086 | 8/1992 |
| WO | WO 94/08467 | 4/1994 |
| WO | WO 98/03671 | 1/1998 |
| WO | WO 98/37179 | 8/1998 |
| WO | WO 98/55625 | 12/1998 |
| WO | WO 99/24448 | 5/1999 |
| WO | WO 02/083870 | 10/2002 |
| WO | WO 2004/087879 | 10/2004 |
| WO | WO 2005/097982 | 10/2005 |

OTHER PUBLICATIONS

Addy et al. "Dissolved Oxygen and Temperature" Natural Resources Facts, Fact Sheet 96-3, Mar. 1997, 4 pages.
Barclay, "Production of Docosahexaenoic Acid from Microalgae and Its Benefits for Use in Animal Feeds", Simopoulos AP (ed): The Return of w3 Fatty Acids Into the Food Supply. I. Land-Based Animal Food Products and Their Health Effects. World Rev Nutr Diet. Basel, Karger, 1998, vol. 83, pp. 61-76.
Beach et al. Biochimica and Biophysica Acta. 1973. 316:56-65.
Biology and Water Pollution Control, W.B. Saunders Company, Philadelphia, 1971, pp. 51-54.
Calvalier-Smith et al., Thraustochytrids are chromists, not Fungi: 18s rRNA signatures of Heterokonta, Phil. Trans. Royal Soc. London Bio Sciences, vol. 346, pp. 387-397, 1994.

(Continued)

Primary Examiner—Vera Afremova
(74) Attorney, Agent, or Firm—Sheridan Ross P.C.

(57) ABSTRACT

The present invention provides a process for growing eukaryotic microorganisms which are capable of producing lipids, in particular lipids containing polyenoic fatty acids. The present invention also provides a process for producing eukaryotic microbial lipids.

39 Claims, 1 Drawing Sheet

OTHER PUBLICATIONS

Experimental Use Statement (Product Sales Appendix) (Appendix A), 5 pages.
Gaudy et al., in Microbiology for Environmental Scientists and Engineers, McGraw-Hill Book Company, New York, 1980, pp. 217-222.
Goldstein; "Zoosporic Marine Fungi (Thraustochytriaceae and Dermosystidiaceae"; Brooklyn College; Dept. of Biology; 1973, pp. 13-26.
Holden C. Science, Dec. 1998, vol. 282, p. 1983.
Hopwood et al. "Molecular Genetics of Polyketides and its Comparison to Fatty Acid Biosynthesis", Ann. Rev. Genet. 1990, vol. 24, pp. 37-66.
Hutchinson, Microbial polyketide synthases: more and more prolific, Proc Natl Acad Sci U S A. Mar. 30, 1999;96(7):3336-8.
Jones et al.; "Recent Advances in Aquatic Mycology; Chapter 10: Physiology of Marine Phycomycetes";John Wiley & Sons; 1976, pp. 261-278.
Kealy et al.; "Production of a polyketide natural product in nonpolyketide-producing prokaryotic and eukaryotic hosts"; Proc. Natl. Acad. Sci. USA; Jan. 1998; vol. 95; pp. 505-509.
Kendrick et al.; "Lipid formation in the oleaginous Mould Entomophthoro Exitalis Grown in Continuous Culture: Effects of Growth Rate, Temperature and Dissolved Oxygen Tention on Polyunsaturated Fatty Acids"; Appl. Microbial Biotechnol; 1992; vol. 37, pp. 18-22.
Lewis et al.; "The Biotechnological Potential of Thraustochytrials"; Mar Biotechnol (NY); Nov. 1999; vol. 6; pp. 580-587.
Metz et al.; "Production of Polyunsaturated Fatty Acids by Polyketide Synthases in Both Prokaryotes and Eukaryotes"; Science; Jul. 13, 2001; vol. 293; pp. 290-293.
Qiu, Biosynthesis of docosahexaenoic acid (DHA, 22:6-4, 7, 10, 13, 16, 19): two distinct pathways, Prostaglandins Léukot Essent Fatty Acids. Feb. 2003;68(2):181-6.
Science and Technology of Food Industry, Issue No. 6, 1999, pp. 62-63.
Sogin et al., Stramenopiles, 1995. Obtained from http://ag.arizona.edu/tree/eukaryotes/stramenopiles/stramenopiles.html on Mar. 7, 2001.
Wallis et al.; "Polyunsaturated Fatty Acids Synthesis: What Will They Think of Next?"; Trends in Biochemical Sciences; Sep. 2002; vol. 27, No. 9; pp. 467-473.
Wetzel, in Limnology, W.B. Saunders Company, Philadelphia, 1975, pp. 123-125.
Yamauchi et al. J. Ferment. Technol. 1983. vol. 61, No. 3, pp. 275-280.
Yazawa et al.; "Chapter 3: Production of Eicosapentaenoic Acid from Marine Bacteria"; Sagami Chemical Research Center; 1992; pp. 29-51.
YSI 550A Dissolved Oxygen Instrument specification sheet, date unknown, 2 pages.
YSI DO 200 Dissolved Oxygen/Temperature instruments specification sheet, copyright 2002, 2 pages.
Answer to Complaint and Counterclaims by Nutrinova Inc. and Nutrinova Nutrition Specialties and Food Ingredients GMBH, dated Oct. 24, 2003, pp. 1-10.
Answer to Second Amended Complaint and Counterclaims, dated Jul. 25, 2005, at pp. 1-5, 9-10, 15-18, 23-25.
Communication under Rule 51(4) EPC (notification that the Examining Division intends to grant a European patent), for European Application Ser. No. 01903376.0, dated Jun. 23, 2006, 38 pages.
Complaint and Demand for Jury Trial in Civil Action No. 03-896, dated Sep. 23, 2003, pp. 1-5.
Craig Weaver strain development laboratory notebooks labeled CW00, CW01, CW02, CW03, CW04, and CW05, dated Jul. 1995 through Jan. 1999, 546 pages.
Decision to grant a European patent for European Application Ser. No. 01903376.0, dated Sep. 6, 2007, pp. 1-2.
Defendant Nutrinova's Third Set of Interrogatories (Nos. 1-12), dated Aug. 22, 2005, at pp. 1-4 and Exhibit A. (Includes Additional Documents Cited: MTK 025138; MTK025118; MTK025143-45; MTK024519-21; MTK027892; MTK027895; MTK024102; MTK024088; MTL024103-04; MTK024171-72; MTK024177-79; MTK024188; MTK02455-28; MTK031762; MTK024271-73; MTL024275; MTK024308; MTK024311-12; MTK024490; MTK024492; MTK026654; MTK026657; MTK026778; MTK26781; MTK 025245; MTK0252248-49; MTK025274; MTK025318; MTK25326-27; MTK025385-86; MTK025388; MTK033821-22; MTK033853-54; MTK33865; MTK033894; MTK027110-112; MTK27128-29; MTK026934-35; MTK026940; MTK026950-51; MTK027185-186; MTK027190; MTK027196-97; MTK027245-46; MTK027249; MTK027256-57; MTK027619-20; MTK027629-30; MTK038660.1-70; MTK037914; MTK037917-18; MTK025744; MTK025748; MTK025756-57; MTK025789-90; MTK025801-02; MTK25834; MTK025844-45; MTK025867; MTK025907-08; MTK026237; MTK026243; MTK026249-50; MTK025919; MTK025924; MTK025931-32; MTK026043; MTK026048; MTK026055-56; MTK026022; MTK06008-09; MTK026091; MTK026105-106; MTK026152; MTK026157; MTK026164-65; MTK026338; MTK026347-49; MTK026421; MTK026428-49; MTK026430; MTK026512; MTK026518; MTK026525-26; MTK026588; MTK026594-96; MTK026598.).
Defendants' 2nd Supplemental Responses and Objections to Plaintiff's Interrogatories Nos. 1, 3, and 4, dated Jan. 26, 2006, at pp. 1-4, 20-24.
Defendants' 3d Supplemental Responses and Objections to Plaintiff's Interrogatories Nos. 3 and 4, Corrected Version, dated Jan. 30, 2006, at pp. 1-3, 23-28.
Defendants' Responses and Objections to Plaintiff's [Martek's] First Set of Interrogatories (Nos. 1-8), dated Mar. 29, 2005, at pp. 1-4, 6, 15-23.
Defendants' Supplemental Responses and Objections to Plaintiff's Interrogatories Nos. 1-4, dated Jun. 2, 2006, at pp. 1-4, 6-8, 15-16, 38-39, 47-48.
Defendants' Trial Brief, dated Aug. 14, 2006, pp. 1-17.
DHA Project Review Technical Meeting w/ OmegaTech dated Feb. 12, 1999, 25 pages.
Email dated Jul. 28, 1999 from Sam Zeller, numbered OTB009229-OTB009230, 2 pages.
Email dated Jul. 28, 1999 from Sam Zeller, numbered OTB009231-OTB009232, 2 pages.
European Examination Report for European Application Ser. No. 01903376.0, issued on Oct. 21, 2005, 3 pages.
Examination Report for European Application Ser. No. 01903376.0, dated Nov. 7, 2006, pp. 1-3.
Experimental data by Joseph Pfeifer, 14 pages.
Expert Report of Dr. David Porter, dated Mar. 6, 2006, pp. 1-4, 8-11.
Expert Report of Dr. Owen Ward, dated Mar. 6, 2006, pp. 1-4, 32-42, and 49. (Includes Additional Documents Cited : MTK059751; MTK059704; MTK059985; MTK59658; MTK059667-8; MTK060034-35; MTK059720; MTK059750; MTK059660; MTK059652; MTK059629-814; MTK059984-60051.).
First Amended Answer to Complaint and Counterclaims, Affirmative Defenses, Counterclaims, and Demand for Jury Trial, dated Oct. 19, 2004, at pp. 1, 3, 8-11, 15-16.
First Amended Complaint, dated Jan. 12, 2005 (filed Jul. 19, 2005), at pp. 1-6 and Exhibit A.
Fourth Amended Complaint, dated Apr. 20, 2006 (filed Apr. 21, 2006), at pp. 1-6.
Initial Disclosures of Plaintiff Martek Pursuant to Fed. R. Civ. P. 26(1)(1), dated Feb. 18, 2005 at pp. 1-3, 6-7.
Memorandum and Order dated Oct. 30, 2007 in Civil Action No. 03-896-GMS, 36 pages.
Memorandum dated Feb. 13, 1998 from Wayne Sander to Sam Zeller, 28 pages.
Memorandum dated Jul. 29, 1999 from Craig Ruecker to Sam Zeller and Sandy Diltz, 14 pages.
Order Construing the Terms of U.S. Patent Nos. 5,340,594; 5,698.244; 6.410.281; 6,451,567; 6,607,900, dated Dec. 12, 2005, at pp. 1, 3-4.
Plaintiff Martek's Responses and Objections to Defendant Nutrinova's Third Set of Interrogatories, dated Dec. 7, 2006, at pp. 1-11 and Exhibit A (Includes Additional Documents Cited; MTK026654-57; MTK026934-35; MTK026950-51; MTK027110-12; MTK027128-29; MTK027185-86; MTK027196-97; MTK027245-46; MTK027256-57; MTK025248-49.

Plaintiff Martek's Supplemental Responses and Objections to Defendant Nutrinova's Third Set of Interrogatories (Nos. 10-12), dated Jan. 27, 2006, at pp. 1-5.
Project file entitled "Weaver Project" relating to the HD1 process and the development of the N230D strain, 139 pages.
Reply to First Answer and Counterclaims, Affirmative Defenses, Counter-Counterclaims, and Demand for Jury Trial, dated Nov. 2, 2004, at pp. 1-4, 7.
Reply to the European Examination Report for European Application Ser. No. 01903376.0, dated Mar. 3, 2006.
Second Amended Complaint, dated Jul. 25, 2005, at pp. 1-7 and Exhibit A.
Strain Improvement for Production of Highly-Unsaturated Fatty Acids: A Proposal by Craig Weaver dated Apr. 1994, 19 pages.
Third Amended Complaint, dated Aug. 24, 2005, at pp. 1-7 and Exhibit A.
Third Party Observations filed in European Application Ser. No. 01903376.0 on Feb. 28, 2005, 69 pages.
Transcript of Deposition of Craig M. Ruecker, dated Feb. 8, 2006 at: pp. 1 to 2; p. 15, I. 12 to p. 16, I. 24; p. 28, I. 17 to p. 36, I. 9; p. 38, I. 8 to p. 45, I. 25; p. 50, I. 1 to p. 53, I. 25; p. 55, I. 3 to p. 73, I. 25; p. 74, I. 11 to p. 84, I. 22; p. 85, I. 3 to 8; p. 85, I. 17 to p. 96, I. 12; p. 97, I. 17 to p. 110, I. 11; p. 112, I. 9 to p. 127, I. 8; p. 127, I. 22 to p. 130, I. 18; p. 131, I. 14 to p. 138, I. 20; p. 142, I. 7 to p. 148, I. 15; p. 151, I. 8 to p. 157, I. 2; p. 159, I. 11 to p. 161, I. 20; p. 163, I. 22 to p. 205, I. 16; p. 206, I. 7 to p. 217, I. 7 to p. 217, I. 7; and Defendant's Deposition Exhibit Nos. 70 to 95, 97 to 113; 115; 121 to 124; 126 to 166.
Transcript of Deposition of Gary J. Connell, dated Feb. 1, 2006 at: p. 1 to p. 7; p. 77; p. 85, 1.13 to p. 94, I. 5; p. 102 I. 18 to p. 103, I. 16; p. 105 to p. 109, I. 11; p. 109, I. 24 to p. 173; and Defendant's Deposition Exhibit Nos. 66 and 58.
Transcript of Deposition of George Thomas Veeder, III dated Feb. 10, 2006 at: p. 1 top to p. 7, 1.1; p. 34, 111 to p. 36, 1.21; p. 38, 1.22 to p. 77, 1.10; p. 1.44, 1.8 to p. 178, 1.21; and Defendant's Deposition Exhibit Nos. 181 and 184.
Transcript of Deposition of Jon M. Hansen, Ph.D., dated Jan. 27, 2006 at: p. 1 to p.4, I. 22; p. 7 I. 12 to p.8, I. 23; p. 57, I. 8 to p. 97, I. 15; p. 120, I. 9 to p. 127, I. 9; p. 129 I. 1, to p. 136, I. 9; and Defendant's Deposition Exhibit Nos. 62 and 63.
Transcript of Deposition of Michael J. Tompkins, dated Jan. 23, 2006 at: p. 1 to p.2; p.4, 1 to p.5, I 7; p. 93, I. 10, to p. 111, I. 2; p. 113, I. 12, to p. 115, I. 3.
Transcript of Deposition of Peter J. Mirrasoul, dated Feb. 7, 2006 at: p. 1 to p. 8, I. 10; p. 14, 14 to p. 70 I. 4; and Defendant's Deposition Exhibit Nos. 69, 72 and 73.
Transcript of Deposition of William Robert Barclay, Jr., Ph.D., dated Jan. 24 and 25, 2006 at: p. 1 to 4; p. 27, I. 16 to p.33, 1. 15; p. 159, I. 10, to p. 186, I. 23; p. 274, I. 1, to p. 340, 5; and Defendant's Deposition Exhibit No. 28.
"Invoice/Production Record Table", including Binder 1, Tab 3; Binder 1, Tab 4; Binder 1, Tab 6; Binder 1, Tab 7; Binder 1, Tab 8; Binder 1, Tab 10; Binder 1, Tab 11; Binder 1, Tab 13; Binder 1, Tab 14; Binder 2, Tab 2; Binder 2, Tab 3; Binder 2, Tab 5; Binder 2, Tab 7; Binder 2, Tab 8; Binder 2, Tab 9; Binder 2, Tab 13; Binder 2, Tab 15; Binder 2, Tab 16; Binder 2, Tab 22; Binder 2, Tab 23; Binder 2, Tab 95; Binder 2, Tab 98; Binder 3, Tab 64; Binder 3, Tab 65; Binder 3, Tab 66; Binder 3, Tab 67; Binder 3, Tab 68; Binder 3, Tab 69; Binder 3, Tab 70; Binder 3, Tab 71; Binder 3, Tab 72; Binder 3, Tab 73; Binder 3, Tab 74; Binder 3, Tab 75; Binder 3, Tab 76; Binder 3, Tab 77; Binder 3, Tab 78; Binder 5; Binder, Tab 61; Binder 6, Tab 66; Binder 6, Tab 67; Binder 6, Tab 68; Binder 6, Tab 69; Binder 6, Tab 70; Binder 6, Tab 71; Binder 6, Tab 72; Binder 6, Tab 75; Binder 6, Tab 76; Binder 6, Tab 77; Binder 6, Tab 89; Binder 6, Tab 90; Binder 7, Tab 25; Binder 7, Tab 26; Binder 7, Tab 27; Binder 7, Tab 28; Binder 7, Tab 30; Binder 7, Tab 31; Binder 7, Tab 33; Binder 7, Tab 34; Binder 7, Tab 35; Binder 7, Tab 36; Binder 7, Tab 37; Binder 7, tab 38; Binder 7, Tab 39; Binder 7, Tab 40; Binder 7, Tab 41; Binder 7, Tab 42; Binder 7, Tab 43; Binder 8, Tab 44; Binder 8, Tab 47; Binder 8, Tab 50; Binder 8, Tab 51; Binder 8, Tab 52; Binder 8, Tab 53; Binder 8, Tab 54; Binder 8, Tab 55; Binder 8, Tab 56; Binder 8, Tab 57; Binder 8, Tab 58; Binder 8, Tab 59; Binder 8, Tab 60; Binder 8, Tab 61; Binder 8, Tab 63; Run No. D98015 (MTK026831-MTK026855, MTK141795-MTK141796, MTK136348-MTK136372); Run No. D98016 (MTK026903- MTK026928, MTK136374- MTK136400, MTK141797-MTK141798); Run No. D98022 (MTK027036- MTK027069, MTK141803- MTK141806, MTK136552- MTK136590); Run No. D98023 (MTK027070-MTK027107, MTK141807-MTK141810, MTK141810, MTK136591-MTK136625); Run No. F98025 (MTK027109-MTK027183, MTK031107-MTK031123, MTK059815, MTK059866-MTK107254, MTK136630-MTK136700); Run No. F98026 (MTK026933-MTK026990, MTK136447-MTK136506, MTK059838-MTK059841); Run No. F98027 (MTK027184-MTK027242, MTK059816-MTK059837, MTK059842-MTK059865, MTK136701-MTK136759); Run No. F98029 (MTK027244-MTK027297, MTK136761-MTK136814); Run No. F98030 (MTK027298-MTK027342, MTK136815-MTK136859; Run No. F98031 (MTK027344-MTK027385, MTK136860-MTK136897); Run No. F98032 (MTK136903-MTK136943, MTK027386-MTK027441); Run No. F98033 (MTK027456-MTK027500, MTK136973-MTK137010, MTK137054-MTK137056); Run No. F98035 (MTK027551-MTK027589, MTK137062-MTK137100, MTK141093); Run No. F98037 (MTK137180-MTK137200); Run No. F98055 (MTK027797-MTK027819, MTK137307-MTK137329); Run No. F98056 (MTK027821-MTK027846, MTK137331-MTK137356); Run No. F98057 (MTK027847-MTK027870, MTK137357-MTK137380); Run No. E99003 (MTK135455-MTK135485, MTK025962-MTK025992, MTK141825-MTK141828); Run No. F99007 (MTK025866-MTK025916, MTK059161-MTK059211, MTK135358-MTK135399); Run No. D98004 (MTK026622-MTK026652); Run No. D98009 (MTK026653-MTK026683, MTK136121-MTK136150); Run No. D80001 (MTK059938-MTK059983); Run No. D80007 (MTK060222-MTK060275); Run No. 95418 (MTK141420, MTK141506); Run No. 95230 (MTK141402); Run No. 70003 (MTK059574-MTK059625); Run No. 96031 (MTK141544-MTK141545); Run No. 96037 (MTK141547-MTK141548); Run No. 96047 (MTK141554-MTK141555); Run No. 96065 (MTK141558-MTK141559); Run No. 96071 (MTK141560-MTK141561); Run No. 96077 (MTK141562-MTK141563); Run No. 96080 (MTK141564-MTK141565); Run No. 96089 (MTK141566-MTK141567); Run No. 96091 (MTK141568); Run No. 96095 (MTK024914-MTK024926, MTK141569, MTK122728-MTK122740); Run No. 96101 (MTK024928-MTK024941, MTK122742-MTK122754, MTK141571-MTK141572); Run No. 96156 (MTK141577-MTK141578); Run No. 96109 (MTK141573-MTK141574); Run No. 96111 (MTK141575-MTK141576); Run No. 96157 (MTK141579-MTK141580); Run No. 96199 (MTK114135-MTK114137, MTK140504-MTK140551); Run No. 96205 (MTK141597-MTK141598); Run No. D80002 (MTK059984-MTK060051); Run No. D80003 (MTK060052.
-MTK060076); Run No. D80004 (MTK060097-MTK060099); Run No. D80005 (MTK060086-MTK060096, MTK060100-MTK060164); Run No. D80006 (MTK060165-MTK060221); Run No. D97103 (MTK032541, MTK141679, MTK023735-MTK023874, MTK121522-MTK121576, MTK121631-MTK121648); Run No. D98010 (MTK026685-MTK026715, MTK136201-MTK136231); Run No. D98012 (MTK026743-MTK026768, MTK141789-MTK141790, MTK136258-MTK136282); and Run No. D98014 (MTK026801-MTK026830, MTK136316-MTK136347).
International Search Report for International (PCT) Patent Application No. PCT/US01/02715, mailed Apr. 20, 2001.
International Preliminary Examination Report for International (PCT) Patent Application No. PCT/US01/02715, completed Aug. 14, 2003.
Corrected International Preliminary Examination Report for International (PCT) Patent Application No. PCT/US01/02715, completed Sep. 9, 2003.
Memorandum dated Jun. 5, 1996 from DiMasi to Roche, Subject: "Monthly Newsletter—May 1996", pp. MTK031724-MTK031726 (Exhibit DX-43).
Project Alpha Highlights and Key Points—(Mar. '98), pp. MTK029718-MTK029725 (Exhibit DX-53).

Project Alpha Highlights and Key Points—(Aug. '98), pp. MTK029675-MTK029685 (Exhibit DX-54).

Memorandum dated Dec. 1, 1995 from Veeder to Bailey, Subject: "Alpha Fermentation Monthly Summary for Nov. 1995", pp. MTK031613-MTK031617 (Exhibit DX-182).

Memorandum dated Jan. 2, 1996 from Veeder to Bailey, Subject: "Alpha Fermentation Monthly Summary for Dec. 1995", pp. MTK031598-MTK031602 (Exhibit DX-183).

Filing of a New Opposition (including translation) for European Patent No. EP 1251744, dated Jul. 3, 2008.

Babij, Effects of Oxygen and Glucose Levels on Lipid Composition of Yeast *Candida utils* Grown in Continuous Culture, vol. XI Biotechnology and Bioengineering at 593-603 (1969).

Plaintiff Martek Biosciences Corporation's Opening Claim Construction Brief, in Civil Action No. 03-089-GMS, dated Oct. 11, 2005, 44 pages.

Defendant Nutrinova's Opening Brief Regarding Claim Construction of Disputed Terms, in Civil Action No. 03-089-GMS, dated Oct. 11, 2005, 39 pages.

Plaintiff Martek Biosciences Corporation's Answering Claim Construction Brief, in Civil Action No. 03-089-GMX, dated Nov. 2, 2005, 47 pages.

Defendant Nutrinova's Reply Brief in Response to Plaintiff Martek's Opening Claim Construction Brief, in Civil Action No. 03-089-GMS, dated Nov. 2, 2005, 24 pages.

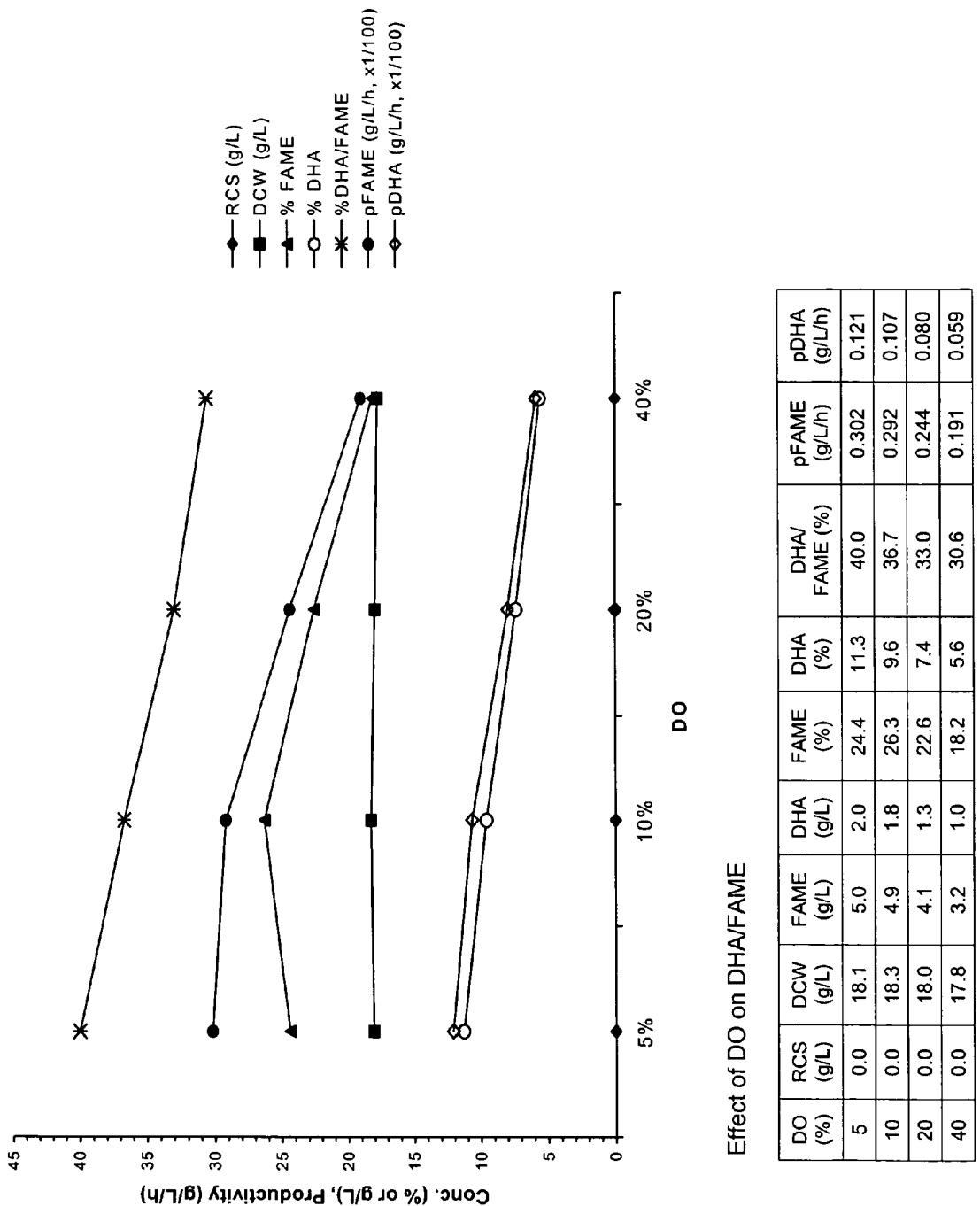
Effect of DO on DHA/FAME

ENHANCED PRODUCTION OF LIPIDS CONTAINING POLYENOIC FATTY ACID BY VERY HIGH DENSITY CULTURES OF EUKARYOTIC MICROBES IN FERMENTORS

CROSS REFERENCE TO RELATED APPLICATIONS

The present application is a continuation of U.S. patent application Ser. No. 10/371,394, filed Feb. 21, 2003, which is a continuation of U.S. patent application Ser. No. 09/771,352, filed Jan. 26, 2001, now U.S. Pat. No. 6,607,900, which claims the benefit of priority under 35 U.S.C. §119(e) from Provisional Patent Application Ser. No. 60/178,588, filed on Jan. 28, 2000. Each of the foregoing applications is incorporated herein by reference in its entirety.

FIELD OF THE INVENTION

The present invention is directed to a novel process for growing microorganisms and recovering microbial lipids. In particular, the present invention is directed to producing microbial polyunsaturated lipids.

BACKGROUND OF THE INVENTION

Production of polyenoic fatty acids (fatty acids containing 2 or more unsaturated carbon-carbon bonds) in eukaryotic microorganisms is generally known to require the presence of molecular oxygen (i.e., aerobic conditions). This is because it is believed that the cis double bond formed in the fatty acids of all non-parasitic eukaryotic microorganisms involves a direct oxygen-dependent desaturation reaction (oxidative microbial desaturase systems). Other eukaryotic microbial lipids that are known to require molecular oxygen include fungal and plant sterols, oxycarotenoids (i.e., xanthophyls), ubiquinones, and compounds made from any of these lipids (i.e., secondary metabolites).

Eukaryotic microbes (such as algae; fungi, including yeast; and protists) have been demonstrated to be good producers of polyenoic fatty acids in fermentors. However, very high density cultivation (greater than about 100 g/L microbial biomass, especially at commercial scale) can lead to decreased polyenoic fatty acid contents and hence decreased polyenoic fatty acid productivity. This may be due in part to several factors including the difficulty of maintaining high dissolved oxygen levels due to the high oxygen demand developed by the high concentration of microbes in the fermentation broth. Methods to maintain higher dissolved oxygen level include increasing the aeration rate and/or using pure oxygen instead of air for aeration and/or increasing the agitation rate in the fermentor. These solutions generally increase the cost of lipid production and can cause additional problems. For example, increased aeration can easily lead to severe foaming problems in the fermentor at high cell densities and increased mixing can lead to microbial cell breakage due to increased shear forces in the fermentation broth (this causes the lipids to be released in the fermentation broth where they can become oxidized and/or degraded by enzymes). Microbial cell breakage is an increased problem in cells that have undergone nitrogen limitation or depletion to induce lipid formation, resulting in weaker cell walls.

As a result, when lipid producing eukaryotic microbes are grown at very high cell concentrations, their lipids generally contain only very small amounts of polyenoic fatty acids. For example, the yeast *Lipomyces starkeyi* has been grown to a density of 153 g/L with resulting lipid concentration of 83 g/L in 140 hours using alcohol as a carbon source. Yet the polyenoic fatty acid content of the yeast at concentration greater than 100 g/L averaged only 4.2% of total fatty acids (dropping from a high of 11.5% of total fatty acid at a cell density of 20-30 g/L). Yamauchi et al., *J. Ferment. Technol.*, 1983, 61, 275-280. This results in a polyenoic fatty acid concentration of only about 3.5 g/L and a polyenoic fatty acid productivity of only about 0.025 g/L/hr. Additionally, the only polyenoic fatty acid reported in the yeast lipids was C18:2.

Another yeast, *Rhodotorula glutinus*, has been demonstrated to have a lipid productivity of about 0.49 g/L/hr, but also a low overall polyenoic fatty acid content in its lipids (15.8% of total fatty acids, 14.7% C18:2 and 1.2% C18:3) resulting in a polyenoic fatty acid productivity in fed-batch culture of only about 0.047 g/L/hr and 0.077 g/L/hr in continuous culture.

Present inventors have previously demonstrated that certain marine microalgae in the order Thraustochytriales can be excellent producers of polyenoic fatty acids in fermentors, especially when grown at low salinity levels and especially at very low chloride levels. Others have described Thraustochyrids which exhibit a polyenoic fatty acid (DHA, C22:6n-3; and DPA, C22:5n-6) productivity of about 0.158 g/L/hr, when grown to cell density of 59 g/L/hr in 120 hours. However, this productivity was only achieved at a salinity of about 50% seawater, a concentration that would cause serious corrosion in conventional stainless steel fermentors.

Costs of producing microbial lipids containing polyenoic fatty acids, and especially the highly unsaturated fatty acids, such as C18:4n-3, C20:4n-6, C20:5n3, C22:5n-3, C22:5n-6 and C22:6n-3, have remained high in part due to the limited densities to which the high polyenoic fatty acid containing eukaryotic microbes have been grown and the limited oxygen availability both at these high cell concentrations and the higher temperatures needed to achieve high productivity.

Therefore, there is a need for a process for growing microorganisms at high concentration which still facilitates increased production of lipids containing polyenoic fatty acids.

SUMMARY OF THE INVENTION

The present invention provides a process for growing eukaryotic microorganisms which are capable of producing at least about 20% of their biomass as lipids and a method for producing the lipids. Preferably the lipids contain one or more polyenoic fatty acids. The process comprises adding to a fermentation medium comprising eukaryotic microorganisms a carbon source, preferably a non-alcoholic carbon source, and a nitrogen source. Preferably, the carbon source and the nitrogen source are added at a rate sufficient to increase the biomass density of the fermentation medium to at least about 100 g/L.

In one aspect of the present invention, the fermentation condition comprises a biomass density increasing stage and a lipid production stage, wherein the biomass density increasing stage comprises adding the carbon source and the nitrogen source, and the lipid production stage comprises adding the carbon source without adding the nitrogen source to induce nitrogen limiting conditions which induces lipid production.

In another aspect of the present invention, the amount of dissolved oxygen present in the fermentation medium during the lipid production stage is lower than the amount of dissolved oxygen present in the fermentation medium during the biomass density increasing stage.

In yet another aspect of the present invention, microorganisms are selected from the group consisting of algae, fungi, protists, and mixtures thereof, wherein the microorganisms are capable of producing polyenoic fatty acids or other lipids which requires molecular oxygen for their synthesis. A particularly useful microorganisms of the present invention are eukaryotic microorganisms which are capable of producing lipids at a fermentation medium oxygen level of about less than 3% of saturation.

In still another aspect of the present invention, microorganisms are grown in a fed-batch process. Moreover, Yet still another aspect of the present invention provides maintaining an oxygen level of less than about 3% of saturation in the fermentation medium during second half of the fermentation process.

Another embodiment of the present invention provides a process for producing eukaryotic microbial lipids comprising:

(a) growing eukaryotic microorganisms in a fermentation medium to increase the biomass density of said fermentation medium to at least about 100 g/L;
(b) providing a fermentation condition sufficient to allow said microorganisms to produce said lipids; and
(c) recovering said lipids, wherein greater than about 15% of said lipids are polyunsaturated lipids.

Another aspect of the present invention provides a lipid recovery step which comprises:

(d) removing water from said fermentation medium to provide dry microorganisms; and
(e) isolating said lipids from said dry microorganisms.

Preferably, the water removal step comprises contacting the fermentation medium directly on a drum-dryer without prior centrifugation.

BRIEF DESCRIPTION OF THE DRAWINGS

FIG. 1 is a table and a plot of various lipid production parameters of a microorganism versus the amount of dissolved oxygen level in a fermentation medium.

DETAILED DESCRIPTION OF THE INVENTION

The present invention provides a process for growing microorganisms, such as, for example, fungi (including yeast), algae, and protists. Preferably, microorganisms are selected from the group consisting of algae, protists and mixtures thereof. More preferably, microorganisms are algae. Moreover, the process of the present invention can be used to produce a variety of lipid compounds, in particular unsaturated lipids, preferably polyunsaturated lipids (i.e., lipids containing at least 2 unsaturated carbon-carbon bonds, e.g., double bonds), and more preferably highly unsaturated lipids (i.e., lipids containing 4 or more unsaturated carbon-carbon bonds) such as omega-3 and/or omega-6 polyunsaturated fatty acids, including docosahexaenoic acid (i.e., DHA); and other naturally occurring unsaturated, polyunsaturated and highly unsaturated compounds. As used herein, the term "lipid" includes phospholipids; free fatty acids; esters of fatty acids; triacylglycerols; sterols and sterol esters; carotenoids; xanthophyls (e.g., oxycarotenoids); hydrocarbons; and other lipids known to one of ordinary skill in the art.

More particularly, processes of the present invention are useful in producing eukaryotic microbial polyenoic fatty acids, carotenoids, fungal sterols, phytosterols, xanthophyls, ubiquinones, other compounds which require oxygen for producing unsaturated carbon-carbon bonds (i. e., aerobic conditions), and secondary metabolites thereof. Specifically, processes of the present invention are useful in growing microorganisms which produce polyenoic fatty acid(s) and for producing microbial polyenoic fatty acid(s).

While processes of the present invention can be used to grow a wide variety of microorganisms and to obtain polyunsaturated lipid containing compounds produced by the same, for the sake of brevity, convenience and illustration, this detailed description of the invention will discuss processes for growing microorganisms which are capable of producing lipids comprising omega-3 and/or omega-6 polyunsaturated fatty acids, in particular microorganisms which are capable of producing DHA. More particularly, preferred embodiments of the present invention will be discussed with reference to a process for growing marine microorganisms, in particular algae, such as Thraustochytrids of the order Thraustochytriales, more specifically Thraustochytriales of the genus *Thraustochytrium* and *Schizochytrium*, including Thraustochytriales which are disclosed in commonly assigned U.S. Pat. Nos. 5,340,594 and 5,340,742, both issued to Barclay, all of which are incorporated herein by reference in their entirety. It is to be understood, however, that the invention as a whole is not intended to be so limited, and that one skilled in the art will recognize that the concept of the present invention will be applicable to other microorganisms producing a variety of other compounds, including other lipid compositions, in accordance with the techniques discussed herein.

Assuming a relatively constant production rate of lipids by an algae, it is readily apparent that the higher biomass density will lead to a higher total amount of lipids being produced per volume. Current conventional fermentation processes for growing algae yield a biomass density of from about 50 to about 80 g/L or less. The present inventors have found that by using processes of the present invention, a significantly higher biomass density than currently known biomass density can be achieved. Preferably, processes of the present invention produces biomass density of at least about 100 g/L, more preferably at least about 130 g/L, still more preferably at least about 150 g/L, yet still more preferably at least about 170 g/L, and most preferably greater than 200 g/L. Thus, with such a high biomass density, even if the lipids production rate of algae is decreased slightly, the overall lipids production rate per volume is significantly higher than currently known processes.

Processes of the present invention for growing microorganisms of the order Thraustochytriales include adding a source of carbon and a source of nitrogen to a fermentation medium comprising the microorganisms at a rate sufficient to increase the biomass density of the fermentation medium to those described above. This fermentation process, where a substrate (e.g., a carbon source and a nitrogen source) is added in increments, is generally referred to as a fed-batch fermentation process. It has been found that when the substrate is added to a batch fermentation process the large amount of carbon source present (e.g., about 200 g/L or more per 60 g/L of biomass density) had a detrimental effect on the microorganisms. Without being bound by any theory, it is believed that such a high amount of carbon source causes detrimental effects, including osmotic stress, for microorganisms and inhibits initial productivity of microorganisms. Processes of the present invention avoid this undesired detrimental effect while providing a sufficient amount of the substrate to achieve the above described biomass density of the microorganisms.

Processes of the present invention for growing microorganisms can include a biomass density increasing stage. In the biomass density increasing stage, the primary objective of the fermentation process is to increase the biomass density in the fermentation medium to obtain the biomass density described above. The rate of carbon source addition is typically maintained at a particular level or range which does not cause a significant detrimental effect on productivity of microorganisms. An appropriate range of the amount of carbon source needed for a particular microorganism during a fermentation process is well known to one of ordinary skill in the art. Preferably, a carbon source of the present invention is a non-alcoholic carbon source, i.e., carbon source that does not contain alcohol. As used herein, an "alcohol" refers to a compound having 4 or less carbon atoms with one hydroxy group, e.g., methanol, ethanol and isopropanol. More preferably, a carbon source of the present invention is a carbohydrate, including, but not limited to, fructose, glucose, sucrose, molasses, and starch. Other suitable simple and complex carbon sources and nitrogen sources are disclosed in the above-referenced patents. Typically, however, a carbohydrate, preferably corn syrup, is used as the primary carbon source.

A particularly preferred nitrogen source is inorganic ammonium salt, more preferably ammonium salts of sulfate, hydroxide, and most preferably ammonium hydroxide.

When ammonium is used as a nitrogen source, the fermentation medium becomes acidic if it is not controlled by base addition or buffers. When ammonium hydroxide is used as the primary nitrogen source, it can also be used to provide a pH control. The microorganisms of the order Thraustochytriales, in particular Thraustochytriales of the genus *Thraustochytrium* and *Schizochytrium*, will grow over a wide pH range, e.g., from about pH 5 to about pH 11. A proper pH range for fermentation of a particular microorganism is within the knowledge of one skilled in the art.

Processes of the present invention for growing microorganisms can also include a production stage. In this stage, the primary use of the substrate by the microorganisms is not increasing the biomass density but rather using the substrate to produce lipids. It should be appreciated that lipids are also produced by the microorganisms during the biomass density increasing stage; however, as stated above, the primary goal in the biomass density increasing stage is to increase the biomass density. Typically, during the production stage the addition of the nitrogen substrate is reduced or preferably stopped.

It was previously generally believed that the presence of dissolved oxygen in the fermentation medium is crucial in the production of polyunsaturated compounds by eukaryotic microorganisms including omega-3 and/or omega-6 polyunsaturated fatty acids. Thus, a relatively large amount of dissolved oxygen in the fermentation medium was generally believed to be preferred. Surprisingly and unexpectedly, however, the present inventors have found that the production rate of lipids is increased dramatically when the dissolved oxygen level during the production stage is reduced. Thus, while the dissolved oxygen level in the fermentation medium during the biomass density increasing stage is at least about 8% of saturation, and preferably at least about 4% of saturation, during the production stage the dissolved oxygen level in the fermentation medium is reduced to about 3% of saturation or less, preferably about 1% of saturation or less, and more preferably about 0% of saturation. In one particular embodiment of the present invention, the amount of dissolved oxygen level in the fermentation medium is varied during the fermentation process. For example, for a fermentation process with total fermentation time of from about 90 hours to about 100 hours, the dissolved oxygen level in the fermentation medium is maintained at about 8% during the first 24 hours, about 4% from about $24^{th}$ hour to about $40^{th}$ hour, and about 0.5% or less from about $40^{th}$ hour to the end of the fermentation process.

The amount of dissolved oxygen present in the fermentation medium can be controlled by controlling the amount of oxygen in the head-space of the fermentor, or preferably by controlling the speed at which the fermentation medium is agitated (or stirred). For example, a high agitation (or stirring) rate results in a relatively higher amount of dissolved oxygen in the fermentation medium than a low agitation rate. For example, in a fermentor of about 14,000 gallon capacity the agitation rate is set at from about 50 rpm to about 70 rpm during the first 12 hours, from about 55 rpm to about 80 rpm during about $12^{th}$ hour to about $18^{th}$ hour and from about 70 rpm to about 90 rpm from about $18^{th}$ hour to the end of the fermentation process to achieve the dissolved oxygen level discussed above for a total fermentation process time of from about 90 hours to about 100 hours. A particular range of agitation speeds needed to achieve a particular amount of dissolved oxygen in the fermentation medium can be readily determined by one of ordinary skill in the art.

A preferred temperature for processes of the present invention is at least about 20° C., more preferably at least about 25° C., and most preferably at least about 30° C. It should be appreciated that cold water can retain a higher amount of dissolved oxygen than warm water. Thus, a higher fermentation medium temperature has additional benefit of reducing the amount of dissolved oxygen, which is particularly desired as described above.

Certain microorganisms may require a certain amount of saline minerals in the fermentation medium. These saline minerals, especially chloride ions, can cause corrosion of the fermentor and other downstream processing equipment. To prevent or reduce these undesired effects due to a relatively large amount of chloride ions present in the fermentation medium, processes of the present invention can also include using non-chloride containing sodium salts, preferably sodium sulfate, in the fermentation medium as a source of saline (i. e., sodium). More particularly, a significant portion of the sodium requirements of the fermentation are supplied as non-chloride containing sodium salts. For example, less than about 75% of the sodium in the fermentation medium is supplied as sodium chloride, more preferably less than about 50% and more preferably less than about 25%. The microorganisms of the present invention can be grown at chloride concentrations of less than about 3 g/L, more preferably less than about 500 mg/L, more preferably less than about 250 mg/L and more preferably between about 60 mg/L and about 120 mg/L.

Non-chloride containing sodium salts can include soda ash (a mixture of sodium carbonate and sodium oxide), sodium carbonate, sodium bicarbonate, sodium sulfate and mixtures thereof, and preferably include sodium sulfate. Soda ash, sodium carbonate and sodium bicarbonate tend to increase the pH of the fermentation medium, thus requiring control steps to maintain the proper pH of the medium. The concentration of sodium sulfate is effective to meet the salinity requirements of the microorganisms, preferably the sodium concentration is (expressed as g/L of Na) at least about 1 g/L, more preferably in the range of from about 1 g/L to about 50 g/L and more preferably in the range of from about 2.0 g/L to about 25 g/L.

Various fermentation parameters for inoculating, growing and recovering microorganisms are discussed in detail in U.S. Pat. No. 5,130,242, which is incorporated herein by reference in its entirety. Any currently known isolation methods can be used to isolate microorganisms from the fermentation medium, including centrifugation, filtration, decantation, and solvent evaporation. It has been found by the present inventors that because of such a high biomass density resulting from processes of the present invention, when a centrifuge is used to recover the microorganisms it is preferred to dilute the fermentation medium by adding water, which reduces the biomass density, thereby allowing more effective separation of microorganisms from the fermentation medium.

Preferably, the microorganisms are recovered in a dry form from the fermentation medium by evaporating water from the fermentation medium, for example, by contacting the fermentation medium directly (i. e., without pre-concentration, for example, by centrifugation) with a dryer such as a drum-dryer apparatus, i. e., a direct drum-dryer recovery process. When using the direct drum-dryer recovery process to isolate microorganisms, typically a steam heated drum-dryer is employed. In addition when using the direct drum-dryer recovery process, the biomass density of the fermentation medium is preferably at least about 130 g/L, more preferably at least about 150 g/L, and most preferably at least about 180 g/L. This high biomass density is generally desired for the direct drum-dryer recovery process because at a lower biomass density, the fermentation medium comprises a sufficient amount of water to cool the drum significantly, thus resulting in incomplete drying of microorganisms. Other methods of drying cells, including spray-drying, are well known to one of ordinary skill in the art.

Processes of the present invention provide a lipid production rate of at least about 0.5 g/L/hr, preferably at least about 0.7 g/L/hr, more preferably at least about 0.9 g/L/hr, and most preferably at least about 1.0 g/L/hr. Moreover, lipids produced by processes of the present invention contain polyunsaturated lipids in the amount greater than about 15%, preferably greater than about 20%, more preferably greater than about 25%, still more preferably greater than about 30%, and most preferably greater than about 35%. Lipids can be recovered from either dried microorganisms or from the microorganisms in the fermentation medium. Generally, at least about 20% of the lipids produced by the microorganisms in the processes of the present invention are omega-3 and/or omega-6 polyunsaturated fatty acids, preferably at least about 30% of the lipids are omega-3 and/or omega-6 polyunsaturated fatty acids, more preferably at least about 40% of the lipids are omega-3 and/or omega-6 polyunsaturated fatty acids, and most preferably at least about 50% of the lipids are omega-3 and/or omega-6 polyunsaturated fatty acids. Alternatively, processes of the present invention provides a DHA production rate of at least about 0.2 g of DHA/L/hr, preferably at least about 0.3 g of DHA/L/hr, more preferably at least about 0.4 g of DHA/L/hr, and most preferably at least about 0.5 g of DHA/L/hr. Still alternatively, at least about 25% of the lipid is DHA (based on total fatty acid methyl ester), preferably at least about 30%, more preferably at least about 35%, and most preferably at least about 40%.

Microorganisms, lipids extracted therefrom, the biomass remaining after lipid extraction or combinations thereof can be used directly as a food ingredient, such as an ingredient in beverages, sauces, dairy based foods (such as milk, yogurt, cheese and ice-cream) and baked goods; nutritional supplement (in capsule or tablet forms); feed or feed supplement for any animal whose meat or products are consumed by humans; food supplement, including baby food and infant formula; and pharmaceuticals (in direct or adjunct therapy application). The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs, milk or other products. When fed to such animals, polyunsaturated lipids can be incorporated into the flesh, milk, eggs or other products of such animals to increase their content of these lipids.

Additional objects, advantages, and novel features of this invention will become apparent to those skilled in the art upon examination of the following examples thereof, which are not intended to be limiting.

EXAMPLES

The strain of *Schizochytrium* used in these examples produces two primary polyenoic acids, DHAn-3 and DPAn-6 in the ratio of generally about 3:1, and small amounts of other polyenoic acids, such as EPA and C20:3, under a wide variety of fermentation conditions. Thus, while following examples only list the amount of DHA, one can readily calculate the amount of DPA produced by using the above disclosed ratio.

Example 1

This example illustrates the affect of oxygen content in a fermentation medium on lipid productivity.

Fermentation results of *Schizochytrium* at various levels of dissolved oxygen content were measured. The results are shown in FIG. 1, where RCS is residual concentration of sugar, and DCW is dry-cell weight.

Example 2

This example illustrates the reproducibility of processes of the present invention.

Microorganisms were produced using fermentors with a nominal working volume of 1,200 gallons. The resulting fermentation broth was concentrated and microorganisms were dried using a drum-dryer. Lipids from aliquots of the resulting microorganisms were extracted and purified to produce a refined, bleached, and deodorized oil. Approximately 3,000 ppm of d-1-α-tocopheryl acetate was added for nutritional supplementation purposes prior to analysis of the lipid.

Nine fermentations of *Schizochytrium* were run and the results are shown in Table 1. The dissolved oxygen level was about 8% during the first 24 hours and about 4% thereafter.

TABLE 1

Fed-batch fermentation results for the production of DHA.

| Entry | Age (Hrs) | Yield[1] (g/L) | DHA (%) | FAME[2] (%) | Productivity[3] |
|---|---|---|---|---|---|
| 1 | 100.3 | 160.7 | 17.8 | 49.5 | 0.285 |
| 2 | 99.8 | 172.4 | 19.4 | 51.3 | 0.335 |
| 3 | 84.7 | 148.7 | 14.4 | 41.4 | 0.253 |
| 4 | 90.2 | 169.5 | 19.7 | 53.9 | 0.370 |
| 5 | 99.0 | 164.1 | 12.5 | 38.9 | 0.207 |
| 6 | 113.0 | 187.1 | 19.7 | 47.2 | 0.326 |
| 7 | 97.0 | 153.5 | 13.7 | 41.0 | 0.217 |
| 8 | 92.8 | 174.8 | 16.4 | 48.6 | 0.309 |
| Avg[4] | 97.1 | 166.4 | 16.7 | 46.5 | 0.288 |
| Std[5] | 8.4 | 12.3 | 2.9 | 5.4 | 0.058 |
| CV[6](%) | 8.7 | 7.4 | 17.3 | 11.7 | 20.2 |

[1]actual yield of biomass density.
[2]total fatty acid methyl esters.
[3](grams of DHA)/L/Hr.
[4]average.
[5]standard deviation.
[6]coefficients of variability. Coefficients of variability values below 5% indicates a process which has excellent reproducibility, values between 5% and 10% indicates a process which has good reproducibility and values between 10% and 20% indicates a process which has reasonable reproducibility.

Corn syrup was fed until the volume in the fermentor reached about 1,200 gallons, at which time the corn syrup addition was stopped. The fermentation process was stopped once the residual sugar concentration fell below 5 g/L. The typical age, from inoculation to final, was about 100 hours.

The fermentation broth, i.e., fermentation medium, was diluted with water using approximately a 2:1 ratio to reduce the ash content of the final product and help improve phase separation during the centrifugation step. The concentrated cell paste was heated to 160° F. (about 71° C.) and dried on a Blaw Knox double-drum dryer (42"×36"). Preferably, however, microorganisms are dried directly on a drum-dryer without prior centrifugation.

The analysis result of lipids extracted from aliquots of each entries in Table 1 is summarized in Table 2.

TABLE 2

Analysis of lipids from microorganisms of Table 1.

| Entry | % DHA relative to FAME[1] | Total Lipid % by wt. |
|---|---|---|
| 1 | 36.0 | 72.3 |
| 2 | 37.8 | 70.3 |
| 3 | 34.8 | 61.5 |
| 4 | 36.5 | 74.8 |
| 5 | 32.1 | 52.8 |
| 6 | 41.7 | 67.7 |
| 7 | 33.4 | 49.9 |
| 8 | 33.7 | 61.4 |
| Avg | 35.8 | 63.8 |
| Std.[3] | 3.0 | 9.1 |
| CV[4] (%) | 8.5 | 14.2 |

[1]see Table 1
2. see discussion above
[3]standard deviation
[4]coefficients of variability Coefficients of variability values below 5% indicates a process which has excellent reproducibility, values between 5% and 10% indicates a process which has good reproducibility and values between 10% and 20% indicates a process which has reasonable reproducibility.

Unless otherwise stated, the fermentation medium used throughout the Examples section includes the following ingredients, where the first number indicates nominal target concentration and the number in parenthesis indicates acceptable range: sodium sulfate 12 g/L (11-13); KCl 0.5 g/L (0.45-0.55); $MgSO_4.7H_2O$ 2 g/L (1.8-2.2); Hodag K-60 antifoam 0.35 g/L (0.3-0.4); $K_2SO_4$ 0.65 g/L (0.60-0.70); $KH_2PO_4$ 1 g/L (0.9-1.1); $(NH_4)_2SO_4$ 1 g/L (0.95-1.1); $CaCl_2.2H_2O$ 0.17 g/L (0.15-0.19); 95 DE corn syrup (solids basis) 4.5 g/L (2-10); $MnCl_2.4H_2O$ 3 mg/L (2.7-3.3); $ZnSO_4.7H_2O$ 3 mg/L (2.7-3.3); $CoCl_2.6H_2O$ 0.04 mg/L (0.035-0.045); $Na_2MoO_4.2H_2O$ 0.04 mg/L (0-0.045); $CuSO_4.5H_2O$ 2 mg/L (1.8-2.2); $NiSO_4.6H_2O$ 2 mg/L (1.8-2.2); $FeSO_4.7H_2O$ 10 mg/L (9-11); thiamine 9.5 mg/L (4-15); vitamin $B_{12}$ 0.15 mg/L (0.05-0.25) and $Ca_{1/2}$Pantothenate 3.2 mg/L (1.3-5.1). In addition, 28% $NH_4OH$ solution is used as the nitrogen source.

The ash content of the dried microorganisms is about 6% by weight.

Example 3

This example illustrates the effect of reduced dissolved oxygen level in the fermentation medium on the productivity of microorganisms using G-tank scale.

Using the procedure described in Example 2, a 14,000 gallon nominal volume fermentation was conducted using *Schizochytrium*, which can be obtained using isolation processes disclosed in the above mentioned U.S. Pat. Nos. 5,340,594 and 5,340,742. The dissolved oxygen level in the fermentation medium was about 8% during the first 24 hours, about 4% from the 24th hour to the 40th hour and about 0.5% from the 40th hour to the end of fermentation process. Results of this lower dissolved oxygen level in fermentation medium processes are shown in Table 3.

TABLE 3

14,000 gallon scale fermentation of *Schizochytrium*.

| Entry | Age (Hrs) | Yield (g/L) | % DHA | % FAME | % DHA rel. to FAME | DHA Productivity (g of DHA/L/hr) |
|---|---|---|---|---|---|---|
| 1 | 82.0 | 179.3 | 121.7 | 52.4 | 41.4 | 0.474 |
| 2 | 99.0 | 183.1 | 122.3 | 55.0 | 40.5 | 0.412 |
| 3 | 72.0 | 159.3 | — | — | 40.9 | — |
| 4 | 77.0 | 161.3 | — | — | 43.2 | — |
| 5 | 100.0 | 173.0 | 23.9 | 53.3 | 44.9 | 0.413 |
| 6 | 102.0 | 183.3 | 21.6 | 50.8 | 42.6 | 0.388 |
| 7 | 104.0 | 185.1 | 23.7 | 55.0 | 43.1 | 0.422 |
| 8 | 88.0 | 179.3 | 22.3 | 52.6 | 42.4 | 0.454 |
| 9 | 100.0 | 166.4 | 22.5 | 53.5 | 42.1 | 0.374 |
| 10 | 97.0 | 182.6 | 22.8 | 51.6 | 44.1 | 0.429 |
| 11 | 87.5 | 176.5 | 19.8 | 45.6 | 43.5 | 0.399 |
| 12 | 67.0 | 170.8 | 18.8 | 48.1 | 39.1 | 0.479 |
| 13 | 97.0 | 184.9 | 23.2 | 52.7 | 44.0 | 0.442 |
| 14 | 102.0 | 181.9 | 23.6 | 52.9 | 44.6 | 0.421 |
| 15 | 102.0 | 186.9 | 19.9 | 47.8 | 41.8 | 0.365 |
| 16 | 97.0 | 184.4 | 19.6 | 45.5 | 43.0 | 0.373 |
| 17 | 98.0 | 174.7 | 19.7 | 45.1 | 43.7 | 0.351 |
| 18 | 103.5 | 178.8 | 18.3 | 44.5 | 41.2 | 0.316 |
| 19 | 102.0 | 173.7 | 15.8 | 43.1 | 36.7 | 0.269 |
| 20 | 94.0 | 190.4 | 19.3 | 46.9 | 41.1 | 0.391 |
| 21 | 72.0 | 172.5 | 22.8 | 52.8 | 43.2 | 0.546 |
| 22 | 75.0 | 173.1 | 21.0 | 51.7 | 40.8 | 0.485 |
| 23 | 75.0 | 152.7 | 20.3 | 50.3 | 40.4 | 0.413 |
| 24 | 75.5 | 172.5 | 21.9 | 51.7 | 42.3 | 0.500 |
| 25 | 61.0 | 156.4 | 17.3 | 45.7 | 37.8 | 0.444 |
| 26 | 74.5 | 150.6 | 20.2 | 50.1 | 40.2 | 0.408 |
| 27 | 70.5 | 134.3 | 14.8 | 40.6 | 36.6 | 0.282 |
| 28 | 75.5 | 146.1 | 21.3 | 49.7 | 42.8 | 0.412 |
| 29 | 82.0 | 174.3 | 21.4 | 50.4 | 42.5 | 0.455 |
| 30 | 105.0 | 182.3 | 21.7 | 50.7 | 42.8 | 0.377 |
| 31 | 66.0 | 146.2 | 16.4 | 44.6 | 36.7 | 0.363 |
| Avg | 87.2 | 171.5 | 20.6 | 49.5 | 41.6 | 0.409 |
| Std | 13.9 | 14.1 | 2.4 | 3.8 | 2.3 | 0.061 |
| CV | 16.0% | 8.2% | 11.6% | 7.7% | 5.5% | 15.0% |

Example 4

This example illustrates the effect of reduced dissolved oxygen level in the fermentation medium on the productivity of microorganisms on a 41,000 gallon scale.

Same procedure as Example 3 in a 41,000 gallon fermentor was performed. Results are shown in Table 4.

TABLE 4

41,000 gallon scale fermentation of *Schizochytrium*

| Entry | Age (Hrs) | Yield (g/L) | % DHA | % FAME | % DHA rel. to FAME | DHA Productivity (g to DHA/L/hr) |
|---|---|---|---|---|---|---|
| 1 | 75.0 | 116.1 | 17.3 | 46.1 | 37.4 | 0.268 |
| 2 | 99.0 | 159.3 | 17.4 | 47.0 | 37.1 | 0.280 |
| 3 | 103.0 | 152.6 | 16.0 | 47.2 | 33.8 | 0.237 |
| 4 | 68.0 | 136.8 | 17.9 | 45.9 | 39.1 | 0.360 |
| 5 | 84.0 | 142.0 | 17.5 | 47.0 | 37.2 | 0.296 |
| Avg | 85.8 | 141.4 | 17.2 | 46.6 | 36.9 | 0.288 |
| Std | 15.1 | 16.6 | 0.7 | 0.6 | 1.9 | 0.046 |
| CV | 17.5% | 11.8 | 4.2% | 1.3% | 5.2% | 15.8% |

Example 5

This example illustrates the affect of extra nitrogen on the fermentation process of the present invention.

Four sets of 250-L scale fed-batch experiments were conducted using a procedure similar to Example 3. Two control experiments and two experiments containing extra ammonia (1.15× and 1.25× the normal amount) were conducted. Results are shown in Table 5.

TABLE 5

Affects of extra ammonia on fermentation of *Schizochytrium*.

| Age (hrs) | Yield (g/L) | Biomass Productivity | Conversion Efficiency | DHA Content | FAME Content | DHA Productivity |
|---|---|---|---|---|---|---|
| Sugar target: 7 g/L, Base pH set point: 5.5, Acid pH set point: 7.3, 1.0X NH$_3$ ||||||||
| 48 | 178 | 3.71 g/L/hr | 51.5% | 10.7% | 37.8% | 0.40 g/L/hr |
| 60 | 185 | 3.08 g/L/hr | 46.9% | 16.3% | 47.2% | 0.50 g/L/hr |
| 72 | 205 | 2.85 g/L/hr | 45.2% | 17.4% | 47.4% | 0.50 g/L/hr |
| 84 | 219 | 2.61 g/L/hr | 43.8% | 17.1% | 45.5% | 0.45 g/L/hr |
| 90 | 221 | 2.46 g/L/hr | 44.1% | 18.4% | 48.9% | 0.45 g/L/hr |
| Sugar target: 7 g/L, Base pH set point: 5.5, Acid pH set point: 7.3, 1.15X NH$_3$ ||||||||
| 48 | 171 | 3.56 g/L/hr | 55.6% | 12.0% | 36.3% | 0.43 g/L/hr |
| 60 | 197 | 3.28 g/L/hr | 54.6% | 9.4% | 38.4% | 0.31 g/L/hr |
| 72 | 191 | 2.65 g/L/hr | 52.8% | 9.4% | 40.0% | 0.25 g/L/hr |
| 84 | 190 | 2.26 g/L/hr | 52.5% | 10.0% | 42.5% | 0.23 g/L/hr |
| 90 | 189 | 2.10 g/L/hr | 52.2% | 9.2% | 43.3% | 0.19 g/L/hr |
| Sugar target: 7 g/L, Base pH set point: 5.5, Acid pH set point: 7.3, 1.25X NH$_3$ ||||||||
| 48 | 178 | 3.71 g/L/hr | 56.4% | 11.5% | 33.7% | 0.43 g/L/hr |
| 60 | 179 | 2.98 g/L/hr | 48.6% | 10.3% | 36.0% | 0.31 g/L/hr |
| 72 | 180 | 2.50 g/L/hr | 48.8% | 12.0% | 37.6% | 0.30 g/L/hr |
| 84 | 181 | 2.15 g/L/hr | 46.1% | 13.6% | 40.1% | 0.29 g/L/hr |
| 90 | 185 | 2.06 g/L/hr | 45.7% | 12.6% | 40.7% | 0.26 g/L/hr |
| Sugar target: 7 g/L, Base pH set point: 5.5, Acid pH set point: 7.3, 1.0X NH$_3$ ||||||||
| 48 | 158 | 3.29 g/L/hr | 55.7% | 13.1% | 36.5% | 0.43 g/L/hr |
| 60 | 174 | 2.90 g/L/hr | 48.9% | 17.9% | 39.2% | 0.52 g/L/hr |
| 72 | 189 | 2.63 g/L/hr | 45.7% | 21.0% | 39.4% | 0.55 g/L/hr |
| 84 | 196 | 2.33 g/L/hr | 44.1% | 22.4 | 40.1% | 0.52 g/L/hr |
| 90 | 206 | 2.29 g/L/hr | 44.8% | 22.1% | 40.3% | 0.51 g/L/hr |

In general, extra nitrogen has a negative effect on fermentation performance, as significant reductions were observed in the DHA productivity for the two batches where extra ammonia were added. As shown on Table 5, the control batches resulted in final DHA levels of 18.4% and 22.1% versus the 9.2% (1.15× ammonia) and 12.6% (1.25× ammonia) for extra nitrogen supplemented batches.

Example 6

This example shows a kinetic profile of a fermentation process of the present invention.

A 1000 gallon scale fed-batch experiment was conducted using a procedure similar to Example 3. Kinetic profile of the fermentation process is shown in Table 6.

TABLE 6

Kinetic Profile for a 1,000 gallon scale Fed-Batch fermentation of *Schizochytrium*.

| Age (hrs) | Yield (g/L) | Biomass Productivity | Conversion Efficiency | % DHA Content | % FAME Content | DHA Productivity |
|---|---|---|---|---|---|---|
| 24 | 118 | 492 g/L/hr | 78.2% | 7.4 | 18.8 | 0.36 g/L/hr |
| 30 | 138 | 4.60 g/L/hr | 60.3% | 10.6 | 30.9 | 0.49 g/L/hr |
| 36 | 138 | 3.83 g/L/hr | 46.6% | 11.6 | 36.5 | 0.44 g/L/hr |
| 42 | 175 | 4.17 g/L/hr | 49.8% | 13.4 | 41.7 | 0.56 g/L/hr |
| 48 | 178 | 3.71 g/L/hr | 45.1% | 18.7 | 52.8 | 0.69 g/L/hr |
| 48* | 164 | 3.42 g/L/hr | 41.5% | 15.3 | 33.1 | 0.52 g/L/hr |
| 54 | 196 | 3.63 g/L/hr | 45.7% | 16.6 | 51.2 | 0.60 g/L/hr |
| 60 | 190 | 3.17 g/L/hr | 41.7% | 16.9 | 33.9 | 0.54 g/L/hr |
| 72 | 189 | 2.62 g/L/hr | 39.1% | 15.6 | 31.8 | 0.41 g/L/hr |
| 84 | 195 | 2.32 g/L/hr | 38.5% | 16.4 | 32.7 | 0.38 g/L/hr |
| 90 | 200 | 2.22 g/L/hr | 39.0% | 18.8 | 33.3 | 0.42 g/L/hr |
| 90 | 171 | 1.90 g/L/hr | 33.3% | 22.2 | 61.6 | 0.42 g/L/hr** |

*Two separate samples were analyzed at 48 hrs.
**This is for a washed dry-cell weights (DCW) sample. Other reported values are for unwashed samples.

Example 7

This example illustrates affect of the amount of carbon source on productivity.

Three different fermentation processed using the process of Example 3 were conducted using various amounts of carbon source. Results are shown on Table 7.

TABLE 7

Fermentation results for various amounts of carbon source on fermentation of *Schizochytrium*.

| Age (hrs) | Yield (g/L) | Carbon Charge | Conversion Efficiency | % DHA Content | % FAME Content | Productivity (g/L/hr) |
|---|---|---|---|---|---|---|
| 90 | 171 | 51.3% | 33.3% | 22.2 | 61.6 | 0.42 |
| 94 | 122 | 40.5% | 30.1% | 19.1 | 57.3 | 0.25 |
| 59 | 73 | 20.0% | 36.5% | 11.9 | 40.8 | 0.15 |

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and or reducing cost of implementation.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for growing microorganisms of the order Thraustochytriales and producing at least about 20% of their biomass as lipids comprising conducting a fermentation of the microorganisms in a medium comprising a carbon source, microorganisms and a limiting nutrient source:
   wherein earlier during the fermentation the dissolved oxygen content of the fermentation medium is at least about 4% of saturation and later during the fermentation the dissolved oxygen content of the fermentation medium is less than about 3% of saturation;
   wherein the fermentation of the microorganisms in the fermentation medium increases the biomass density of the fermentation medium when the carbon source and limiting nutrient source are present in the fermentation medium and when the dissolved oxygen content of the fermentation medium is at least about 4% of saturation;
   wherein the fermentation of the microorganisms in the fermentation medium produces lipids containing polyenoic fatty acids when the dissolved oxygen content of the fermentation medium is less than about 3% of saturation;
   wherein the process produces at least an average rate of about 0.5 grams of lipids per liter of fermentation medium per hour of the fermentation; and
   wherein at least about 15% of the total lipids produced by the microorganisms are polyunsaturated lipids.

2. The process of claim 1, wherein the process is a fed-batch process.

3. The process of claim 1, wherein the fermentation of the microorganisms in the fermentation medium produces lipids containing polyenoic fatty acids when the dissolved oxygen content of the fermentation medium is less than about 1% of saturation.

4. The process of claim 1, wherein the microorganisms are selected from the group consisting of *Thraustochytrium*, *Schizochytrium*, and mixtures thereof.

5. The process of claim 1, wherein the process produces on average at least about 0.2 grams of docosahexaenoic acid per liter of fermentation medium per hour of the fermentation.

6. The process of claim 1, wherein the process is a batch or continuous process.

7. The process of claim 1, wherein the dissolved oxygen content of the fermentation medium is less than about 3% of saturation when carbon source is added with no or little additional limiting nutrient source to induce nutrient limiting conditions which induces lipid production.

8. The process of claim 1, wherein the fermentation of the microorganisms in the fermentation medium produces lipids containing polyunsaturated lipids when the dissolved oxygen content of the fermentation medium is less than about 1% of saturation.

9. The process of claim 1, wherein the process is conducted for at least 90 hours, wherein the dissolved oxygen level in the fermentation medium is maintained at about 8% during the first 24 hours, about 4% from the 24th hour to the $40^{th}$ hour, and about 0.5% or less from the $40^{th}$ hour to the end of the process.

10. The process of claim 1, wherein the dissolved oxygen level in the fermentation medium is maintained at about 0.5% or less after 40 hours of the process until the end of the process.

11. The process of claim 1, wherein the carbon source comprises a carbohydrate.

12. The process of claim 1, wherein the limiting nutrient source comprises a nutrient source selected from the group consisting of nitrogen sources, phosphate sources, vitamin sources, trace metal sources, major metal sources, silica sources and mixtures thereof.

13. The process of claim 1, wherein the limiting nutrient source comprises a nutrient source selected from the group consisting of a trace metal source and a major metal source selected from the group consisting of sulfate and chloride salts of these metals and mixtures thereof.

14. The process of claim 1, wherein the limiting nutrient source comprises a nitrogen source.

15. The process of claim 1, wherein the limiting nutrient source comprises an inorganic ammonium salt.

16. The process of claim 1, wherein the limiting nutrient source comprises ammonium hydroxide.

17. The process of claim 1, wherein pH of the fermentation medium is controlled by a limiting nutrient source.

18. The process of claim 1, wherein the fermentation medium is at a temperature of at least about 20° C.

19. The process of claim 1, wherein the process produces at least about 15% of the total lipids produced by the microorganisms as docosahexaenoic acid.

20. The process of claim 1, wherein the total amount of omega-3 and omega-6 fatty acids is at least about 20% of the lipids.

21. The process of claim 1, wherein at least about 25% of the lipids is docosahexaenoic acid.

22. The process of claim 1, wherein the microorganisms are capable of producing polyenoic fatty acids or other lipids which can be produced under aerobic conditions.

23. The process of claim 22, wherein the microorganisms produce polyenoic fatty acids or other lipids produced under aerobic conditions.

24. The process of claim 1, wherein the microorganisms are capable of producing polyenoic fatty acids or other lipids which can be produced under aerobic conditions, and wherein the microorganisms are grown in a fed-batch process.

25. The process of claim 24, wherein the microorganisms produce polyenoic fatty acids or other lipids produced under aerobic conditions.

26. The process of claim 1, wherein the microorganisms are capable of producing polyenoic fatty acids or other lipids which can be produced under aerobic conditions and wherein the microorganisms are grown in a fed-batch process.

27. The process of claim 1, wherein the dissolved oxygen in the fermentation medium is controlled.

28. The process of claim 27, wherein the dissolved oxygen in the fermentation medium is controlled by step selected from the group consisting of controlling the amount of oxygen in the head-space of the fermentor and controlling the speed at which the fermentation medium is agitated.

29. The process of claim 1, further comprising:
removing water from the fermentation medium to provide dry microorganisms; and
isolating the lipids from the dry microorganisms, wherein at least about 15% of the microbial lipids are polyunsaturated lipids.

30. The process of claim 1, wherein at least about 15% of the microbial lipids are docosahexaenoic acid.

31. The process of claim 1, further comprising:
treating the fermentation medium to permeabilize, lyse or rupture the microbial cells; and
recovering the lipids from the fermentation medium by gravity separation, with or without the aid of an agent to aid in breaking the lipid/water emulsion wherein at least about 15% of the microbial lipids are polyunsaturated lipids.

32. The process of claim 1, wherein at least about 15% of the microbial lipids are docosahexaenoic acid.

33. The process of claim 1, further comprising:
evaporating water from the fermentation medium without prior centrifugation to provide dry microorganisms; and
isolating the lipids from the dry microorganisms wherein at least about 15% of the microbial lipids are polyunsaturated lipids.

34. The process of claim 33, wherein at least about 15% of the microbial lipids are docosahexaenoic acid.

35. The process of claim 1, wherein the fermentation of the microorganisms in the fermentation medium produces lipids containing polyenoic fatty acids when the fermentation medium has a biomass density of at least about 100 g/l.

36. The process of claim 1, wherein the fermentation of the microorganisms in the fermentation medium produces lipids containing polyenoic fatty acids when the fermentation medium has a biomass density of at least about 150 g/l.

37. The process of claim 1, further comprising recovering lipids from the microorganisms.

38. The process of claim 37, wherein the lipids comprise polyunsaturated lipids.

39. The process of claim 37, wherein the lipids comprise docosahexaenoic acid.

\* \* \* \* \*

UNITED STATES PATENT AND TRADEMARK OFFICE
CERTIFICATE OF CORRECTION

PATENT NO. : 7,579,174 B2
APPLICATION NO. : 11/352421
DATED : August 25, 2009
INVENTOR(S) : Bailey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 332 days.

Signed and Sealed this

Fourteenth Day of September, 2010

David J. Kappos
*Director of the United States Patent and Trademark Office*